(12) United States Patent
Oral et al.

(10) Patent No.: US 8,971,997 B2
(45) Date of Patent: Mar. 3, 2015

(54) NON-CONTACT INFRARED FIBER-OPTIC DEVICE FOR MEASURING TEMPERATURE IN A VESSEL

(75) Inventors: Hakan Oral, Ann Arbor, MI (US); Fred Morady, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 298 days.

(21) Appl. No.: 12/934,008

(22) PCT Filed: Mar. 24, 2009

(86) PCT No.: PCT/US2009/038101
§ 371 (c)(1),
(2), (4) Date: Sep. 22, 2010

(87) PCT Pub. No.: WO2009/120694
PCT Pub. Date: Oct. 1, 2009

(65) Prior Publication Data
US 2011/0028788 A1    Feb. 3, 2011

Related U.S. Application Data

(60) Provisional application No. 61/038,959, filed on Mar. 24, 2008.

(51) Int. Cl.
*A61B 6/00*        (2006.01)
*G01J 5/00*        (2006.01)
(Continued)

(52) U.S. Cl.
CPC .............. *G01J 5/0022* (2013.01); *A61B 1/273* (2013.01); *A61B 5/015* (2013.01); *A61B 5/412* (2013.01); *G01J 5/0025* (2013.01); *G01J 5/02* (2013.01); *G01J 5/0215* (2013.01); *G01J 5/04* (2013.01);
(Continued)

(58) Field of Classification Search
USPC ................ 600/407, 473, 476, 101, 109, 118; 606/1, 2, 3, 7, 10–18
See application file for complete search history.

(56) References Cited

U.S. PATENT DOCUMENTS 4,648,892 A  *  3/1987  Kittrell et al. ................... 65/387
4,953,539 A       9/1990  Nakamura et al.
(Continued)

OTHER PUBLICATIONS

International Search Report from PCT/US2009/038101 dated Oct. 28, 2009.
(Continued)

*Primary Examiner* — James Kish
(74) *Attorney, Agent, or Firm* — Marshall, Gerstein & Borun LLP

(57) ABSTRACT

An infrared fiber-optic device is able to monitor esophageal temperature during an ablation/cryoablation procedure over a volume of interest to sense whether the temperature is too high or too low. The device may include a plurality of optical fibers each with a wide angle lens collectively disposed circumferentially and longitudinally to cover the volume of interest, as the particular region over which undesirable temperature may not be known beforehand. In other examples, the device may include an embedded array of infrared sensors extending sufficiently to encompass a volume of interest. The device may be used as part of a feedback control to regulate and stop operation of the ablation/cryoablation procedure to prevent vessel damage.

22 Claims, 6 Drawing Sheets

(51) Int. Cl.
*A61B 1/273* (2006.01)
*A61B 5/01* (2006.01)
*A61B 5/00* (2006.01)
*G01J 5/02* (2006.01)
*G01J 5/04* (2006.01)
*G01J 5/08* (2006.01)
*A61B 18/02* (2006.01)
*A61B 18/12* (2006.01)
*A61B 18/18* (2006.01)
*A61B 17/00* (2006.01)
*A61B 18/00* (2006.01)

(52) U.S. Cl.
CPC .. *G01J 5/047* (2013.01); *G01J 5/08* (2013.01); *G01J 5/0806* (2013.01); *G01J 5/0809* (2013.01); *G01J 5/0818* (2013.01); *G01J 5/0843* (2013.01); *G01J 5/0846* (2013.01); *A61B 18/0218* (2013.01); *A61B 18/1206* (2013.01); *A61B 18/18* (2013.01); *A61B 2017/00057* (2013.01); *A61B 2017/00061* (2013.01); *A61B 2017/00084* (2013.01); *A61B 2018/00011* (2013.01); *A61B 2018/00488* (2013.01); *A61B 2018/0212* (2013.01); *A61B 2562/0271* (2013.01); *G01J 2005/0081* (2013.01)
USPC ........... 600/473; 600/407; 600/474; 600/475; 600/101; 600/109; 600/118; 606/1; 606/2; 606/3; 606/7

(56) References Cited

U.S. PATENT DOCUMENTS

| | | | |
|---|---|---|---|
| 4,973,848 A | | 11/1990 | Kolobanov et al. |
| 5,380,317 A | | 1/1995 | Everett et al. |
| 5,460,182 A | * | 10/1995 | Goodman et al. ............ 600/342 |
| 5,547,455 A | * | 8/1996 | McKenna et al. ............ 600/113 |
| 5,647,368 A | | 7/1997 | Zeng et al. |
| 5,649,924 A | | 7/1997 | Everett et al. |
| 5,871,449 A | | 2/1999 | Brown |
| 6,134,003 A | | 10/2000 | Tearney et al. |
| 6,197,022 B1 | | 3/2001 | Baker |
| 6,245,026 B1 | * | 6/2001 | Campbell et al. ............. 600/549 |
| 6,370,422 B1 | | 4/2002 | Richards-Kortum et al. |
| 6,501,551 B1 | | 12/2002 | Tearney et al. |
| 6,516,216 B1 | | 2/2003 | Fontenot et al. |
| 6,575,969 B1 | * | 6/2003 | Rittman et al. ................. 606/41 |
| 6,620,189 B1 | | 9/2003 | Machold et al. |
| 6,709,154 B1 | | 3/2004 | Janotte |
| 6,716,178 B1 | | 4/2004 | Kilpatrick et al. |
| 6,740,082 B2 | | 5/2004 | Shadduck |
| 6,821,249 B2 | | 11/2004 | Casscells, III et al. |
| 6,873,868 B2 | * | 3/2005 | Furnish ........................ 600/435 |
| 7,062,306 B2 | | 6/2006 | Benaron et al. |
| 7,081,096 B2 | * | 7/2006 | Brister et al. ................. 600/549 |
| 7,130,047 B2 | | 10/2006 | Chinnock et al. |
| 7,150,745 B2 | | 12/2006 | Stern et al. |
| 7,198,635 B2 | | 4/2007 | Danek et al. |
| 7,264,587 B2 | | 9/2007 | Chin |
| 7,429,261 B2 | | 9/2008 | Kunis et al. |
| 2002/0076178 A1 | * | 6/2002 | Klocek et al. ................. 385/106 |
| 2003/0013936 A1 | * | 1/2003 | Jackson, III ................... 600/104 |
| 2003/0028114 A1 | | 2/2003 | Casscells et al. ............. 600/474 |
| 2003/0114761 A1 | * | 6/2003 | Brown .......................... 600/474 |
| 2003/0233033 A1 | | 12/2003 | Korotko et al. |
| 2005/0154262 A1 | | 7/2005 | Banik et al. |
| 2005/0288654 A1 | | 12/2005 | Nieman et al. |
| 2006/0195014 A1 | | 8/2006 | Seibel et al. |
| 2007/0197919 A1 | | 8/2007 | Krisch et al. |
| 2007/0270717 A1 | * | 11/2007 | Tang et al. .................... 600/585 |
| 2009/0163901 A1 | * | 6/2009 | Fisher et al. ................... 606/16 |

OTHER PUBLICATIONS

Lenox Instrument Company, Inc., Swing Prism Adjustable Borescopes with 360° Orbital Viewing (2005).
Written Opinion from PCT/US2009/038101 dated Sep. 24, 2010.
European Search Report from Application No. 09723635.0 dated Oct. 1, 2012.

* cited by examiner

NON-CONTACT INFRARED FIBER-OPTIC DEVICE FOR MEASURING TEMPERATURE IN A VESSEL

FIELD OF TECHNOLOGY

The invention relates to optical probe devices and, more particularly, to optical probe devices for monitoring temperature in a body vessel.

DESCRIPTION OF RELATED ART

Catheter ablation is an effective method of destroying tissue that lead to cardiac arrhythmias. Radio-frequency (RF) catheter ablation, for example, is commonly used to treat atrial fibrillation (AF) which is the most common heart arrhythmia leading to hospitalization. A catheter is inserted into a patient's heart or other vessel, and heat is applied to a localized region until the tissue in that region has been sufficiently destroyed to abate the arrhythmia. In other applications, cryoablation has also been used to freeze and destroy local tissue Although thermal RF treatments are useful, it is difficult to determine with sufficient accuracy the parameters needed for successful RF treatment. Inexactness in the amount of heat or exposure time of an affected tissue may lead to thermal injury and coagulative necrosis. Radiofrequency catheter ablation of the heart is particularly susceptible to such problems, because the lesion depth within a treatment site and the tissue diameter (and thickness) of adjacent esophageal vessel will vary across patients from a few mms to 10-15 mms. As such, the required available amount of RF energy to treat the heart or aortic vessel is difficult to predict. The acceptable temperature thresholds vary not only based on the treatment vessel but also based on vessels adjacent thereto. This inexactness can be particularly problematic in radiofrequency catheter ablation procedures because the esophagus being immediately adjacent the posterior left atrial wall leaves a distance of 5 mm or less between the esophagus and the endocardial surface of the posterior left atrium. If the temperature is too high given the proximity of the vessels, RF application along the posterior left atrial wall may cause necrosis of the esophageal wall, which may lead to a fistula formation between the atrium (heart) and the esophagus. Such atrioesophageal fistula may lead to infection and sepsis, air and particulate matter emboli to the brain, as well as to strokes and possible to death, if not diagnosed and treated.

To date there have been no effective measures to prevent atrioesophageal fistula formation. The safest method, in fact, is one that avoids the application of RF energy over the entire esophagus. Instead, the esophagus is visualized with a radiopaque material (e.g., Barium) swallowed prior to the procedure. Barium is visible through fluoroscopy during an X-Ray and thus can be used to visually instruct medical personnel when an ablation catheter is right on the esophagus, so that the personnel will know that RF energy is not to be applied and the ablation catheter is to be moved elsewhere. There are limitations, of course. For example, critical target sites are often close to the esophagus, such that the failure to ablate these sites will compromise the efficacy of the procedure. Furthermore, the procedure may not be used for all patients due to the risks of airway protection, for example, during moderate to deep sedation and anesthesia.

Therefore, the inventor found that it was necessary to monitor for development of a temperature rise within the esophagus or vessel during RF ablation in the posterior left atrium, such that when a minimal increase in temperature is noted in the esophagus then RF ablation can be terminated and inadvertent esophageal injury can be prevented.

DETAILED DESCRIPTION

Figure 1A:
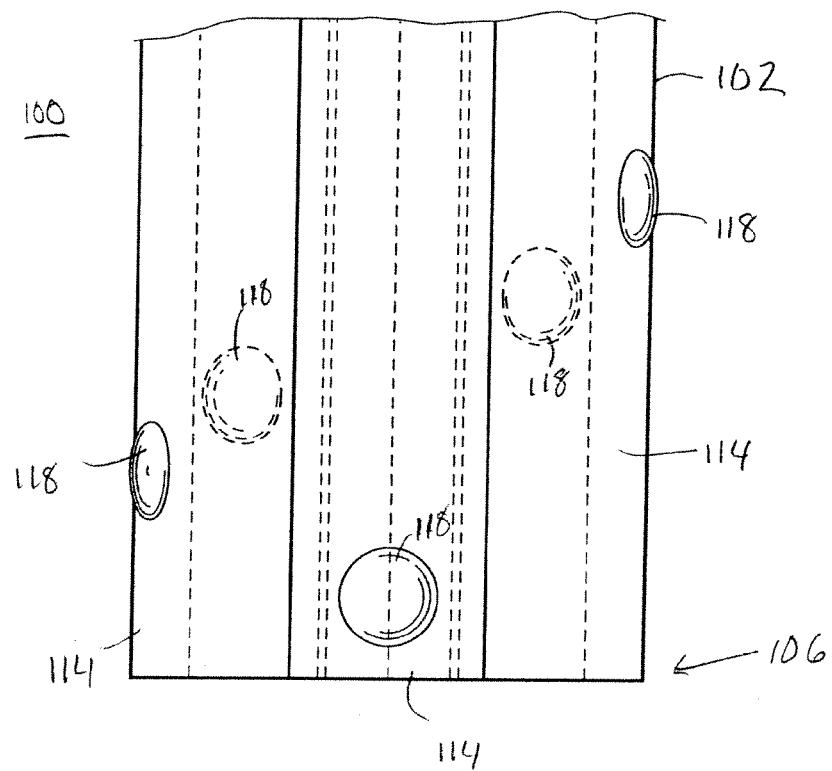
FIG. 1A illustrates a distal portion of an fiber-optic assembly portion of an infrared sensor.

Generally speaking, various body sensor apparatuses are described to monitor temperature changes within a body vessel, such as the esophagus. Many conventional temperature sensors (RTD, thermistors and thermocouples) depend upon direct tissue contact or very close physical contact to sense temperature. The present application allows the monitoring of spot or "point" measuring as well as large areas of temperature monitoring through the use of non-contact temperature sensors. This is particularly important for hollow vessels like the esophagus where conventional sensors are limited because such sensors cannot physically contact all walls at all times.

The present application also describes techniques that can sense temperature changes along a length and around a partial or full circumference of a body cavity or lumen structure. This ability to measure temperature over an area of interest may be particularly beneficial within the esophagus during RF catheter ablation treatments of the left atrium, because the two abut over a length of up to 5-6 cm and over a width of up to 4-5 cm. Therefore, by being able to measure the thermal radiation or portion of the infrared part of the electromagnetic spectrum over a small "point" to a large field of field, the margin of safety is greatly improved. Any temperature increase is recognized within the entire lumen of the esophagus and without necessarily having direct contact with the lumen.

In some examples, fiber-optic temperature sensors are able to sense temperature, and more particularly temperature changes, based on the amount of thermal electromagnetic radiation received (e.g., infrared radiation detected) from the esophageal wall and directed to a high-resolution infrared sensor. In some examples, that sensor may be an infrared camera able to produce a 2-D and or 3-D temperature image map of the region of interest. In other examples, as discussed herein, the sensor may be an infrared sensor that determines high/low peak temperature values, average temperature values, changes in temperature over time or over a spatial distance, etc. The fiber-optic temperature sensors are formed of a probe that may be attached to the infrared sensor through a lightproof attachment. The probe can be covered with a coating susceptible to gas sterilization and thus usable multiple times by medical personnel. Yet, in other examples, the probe can be a limited use or single use device.

The probes may have both side-view and end-view capabilities that together offer 360° infrared sensing within a vessel. This viewing capacity may be achieved, for example, by using a probe formed of multiple fiber-optic channels each with a wide-angle, side view lens as a light coupler. These fiber-optic channels and side view lenses may be organized such that a minimum length (e.g., 5 cm) of the vessel will be visible to the sensor device. In other examples, the instrument may be that of a swing-prism adjustable scope that uses a rotating lens to measure a "point" along the lumen to 360° orbital scan. In any of these examples, the probe device may be used to measure infrared radiation within the esophagus and just behind the posterior left atrium, where RF energy is often applied during catheter ablation of atrial fibrillation and other arrhythmias.

The infrared energy collected by the fiber-optic channels forming the probe may be directed to the infrared sensor by angled mirrors within the fiber-optic channels. A computer coupled to receive the infrared data from the sensors is taken through a calibration process during which baseline infrared measurements are acquired prior to the application of radiofrequency energy. Once calibration (or a similar technique) is finished, infrared measurement may occur. In some examples, the infrared sensor is controlled to sample the vessel at an adjustable rate from 1 Hz to 1000 Hz. Software executed on the computer stores thresholds for temperature levels, such that if the infrared sensor detects an infrared signal corresponding to a temperature above the thresholds, the operating personnel may be notified or the system may automatically perform a safety function (i.e., stop ablations, deliver a fluid flush to the inside of the lumen). The computer system may allow custom spatiotemporal thresholds that measure and react to changes in temperature as well. It should be noted that although absolute temperature measurements may be provided, the system primarily depends on a relative increase in temperature compared to a baseline and/or to adjacent pixels.

Instead of having a bundle of fiber-optic channels that communicate the collected 360° of infrared data to an external infrared sensor, in some examples the temperature sensing probe has an infrared sensing apparatus placed at the distal end of the probe where opto-electric conversion occurs before signals are electronically transmitted to a data processing unit. One such design includes an array of fiber-optic channels, lenses and mirrors. Infrared radiation is transmitted to an infrared sensor array embedded within the distal end of the probe and positioned perpendicular to the long axis of the probe. Electrical signals from these sensors are then transmitted through the long axis of the probe to a main computer.

Another design includes an array of infrared sensors built circumferentially along the distal end of the probe to cover up to 360° and extending along an axial length of the probe. Infrared radiation is relayed directly to these sensors, with or without the use of wide angle lenses and without the need for internal reflectors. After conversion of the infrared radiation, signals are transmitted electronically to a main computer.

Any of the endoscopic devices and probes described herein may be implemented in re-sterilizable or disposable forms, biologically inert for the applications of use.

Examples are described below in reference to particular applications. However, it will be understood that these examples may be useful in any number of medical procedures. Cryoablation, for example, has also been used to destroy cardiac tissue to eliminate arrhythmogenic foci. The devices described herein may be used during cryoablation to monitor for decreases in temperature to prevent esophageal injury. The devices can also be used monitoring temperature changes during ablation using different forms of energy such ultrasound, microwave, laser, or conductive heating through use of a balloon that contains heated solution, etc.

The applications may be used in any number of bodily cavities or vessels, such as any part of the gastrointestinal tract including esophagus, stomach, intestines, colon, rectum, etc, as well as genitourinary tract such as the bladder, uterus, prostate, etc.

Figure 1B:
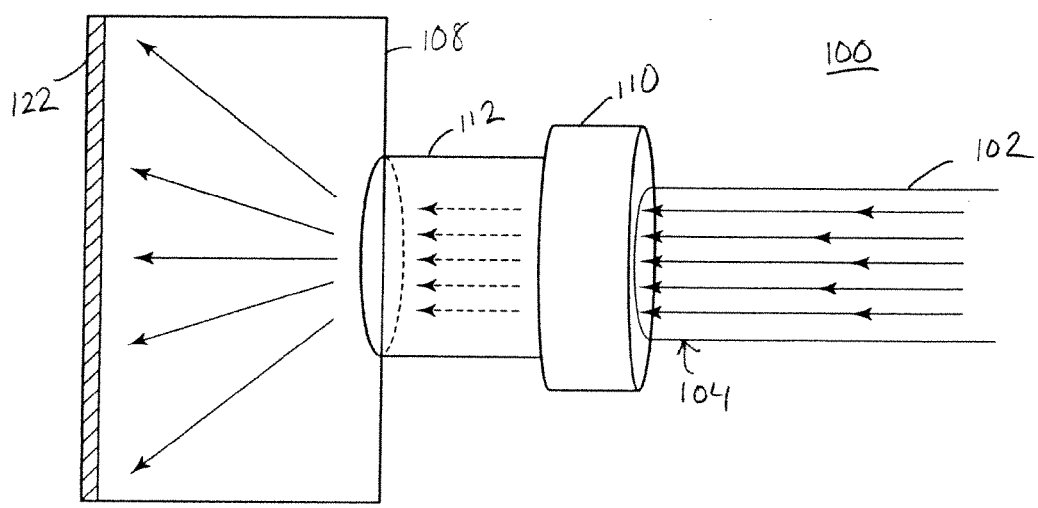
FIG. 1B illustrates a proximal portion of the fiber-optic assembly portion of FIG. 1 and connected to an infrared sensor.

FIGS. 1A and 1B illustrate different portions of an infrared sensor device in the form of an endoscopic device 100 capable of measuring infrared radiation in a vessel. The device 100 includes two main portions, a fiber-optic channel assembly 102 that extends from a proximal end 104 (FIG. 1B) to a distal end 106 of the device 100. The other main portion is a sensor assembly 108 coupled to the fiber-optic channel assembly 102 through an attachment apparatus 110 and dispersing lens 112. The assembly 102 collects infrared radiation from a vessel's region of interest at the distal end 106 and communicates that infrared radiation to the sensor assembly 108. In the illustrated example, the fiber-optic channel assembly 102 is formed of a bundle of individual fiber-optic channels 114, each adjacent at least two other channels to allow for a continuous or nearly continuous viewing region over the circumference of the assembly 102.

The attachment apparatus 110 may be integrally formed to fixedly or releasably attach the fiber-optic channel assembly 102 with the dispersing lens 112. The attachment apparatus 110 may be formed as part of a housing member for the fiber-optic channel assembly 102, for example. In other examples, the attachment apparatus 110 may be a cap for the fiber-optic channel assembly 102. In either example, the attachment apparatus 110 may be glued, fused, or otherwise attached to the fiber-optic channel assembly 102. The particular ferrule shape of the attachment apparatus 110 will very with the application and desired attachment to the dispersing lens 112—although, the shape should be compatible with multimode operation and coupling to the lens 112.

Figure 2A:
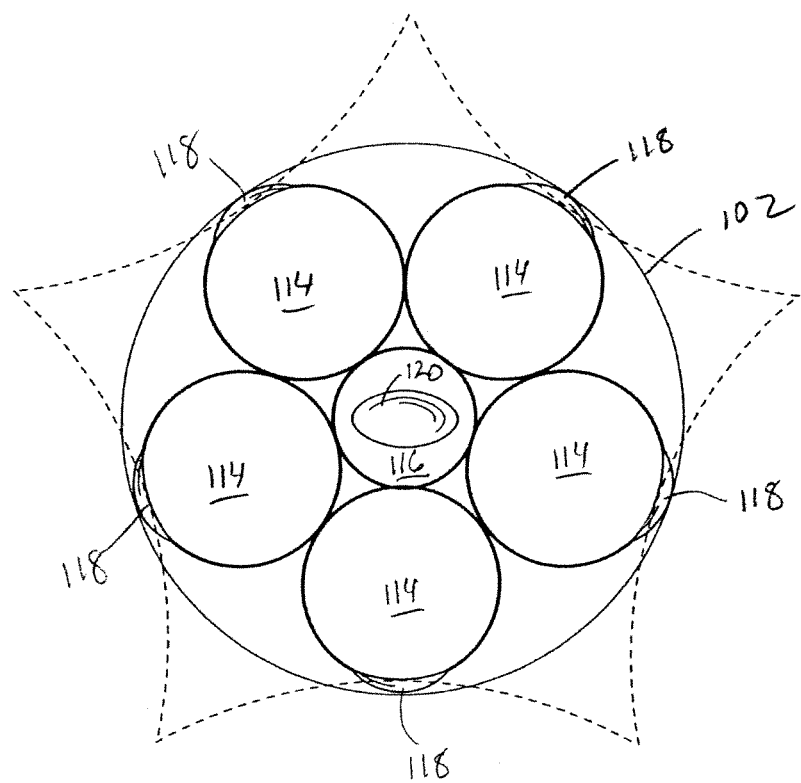
FIG. 2A illustrates an end view of the fiber-optic assembly portion of FIG. 1A.

FIG. 2A shows the fiber-optic channels 114 surrounding a center fiber-optic channel 116 that also extends from the distal end 106 to the proximal end 104. The channels 114 are modified optical fibers that may be formed of typical optical fiber materials, such as silica glass, fluorozirconate, fluoroaluminate, and chalcogenide glasses, or compositions thereof. Yet other suitable materials exhibiting low absorption loss for infrared radiation exist, including optical fiber plastics. For measuring thermal conditions within a body cavity, such as an esophagus, infrared radiation in the near infrared and above region may be detected, for example, radiation at approximately 900 nm or above.

The fiber-optic channel assembly 102 is able to collect infrared radiation around a side view of the device 102 along both an axial length and the entire circumference of the device 100. In this way and as further discussed below, the fiber-optic channel assembly 102 is able to detect infrared radiation over a two dimensional cylindrical region of interest. To achieve this expanded region of interest, each of the fiber-optic channels 114 includes an access window 118 for collecting infrared radiation from the vessel within which the device 100 has been placed.

In the illustrated example, the access windows 118 are wide angled lenses each disposed on the periphery of one of the fiber-optic channels 114 to collect infrared radiation along the side view. As shown by the dashed lines of FIG. 2A indicating the field of view, in a preferred example, wide angled lenses are used as the access windows 118 to allow the assembly 102 to collect infrared radiation from the entire circumference around the assembly. In this way, more accurate infrared radiation detection can occur. The access windows 118 are shown as concave lenses. However in other examples, the lenses may be convex lenses or lens systems, diffractive lenses, or other optical elements.

As shown in FIG. 1A, the wide angle lenses 118 are preferably staggered both longitudinally along the axis of the fiber-optic channel assembly 102 and circumferentially about the circumference of that assembly 102 to collect radiation over a three dimensional area of the side view. In this way, the lenses 118 follow a helical or near helical path wrapping around the circumference of the assembly 102.

By longitudinally staggering the wide angle lenses 118 along an axis, the assembly 102 is able to collect radiation over a length of a body cavity or lumen instead of merely at just a singular side view region. This allows for more accurate detection of infrared radiation and more accurate determination of whether for example a body cavity or lumen is experiencing excessive heat. The wide angle lenses 118 are staggered circumferentially about the device 102 by having one wide angle lens disposed on each of the fiber-optic channels 114 in a bundle configuration. This allows the assembly 102 to sense infrared radiation not only along a length of a body cavity or lumen but around the entire inner wall of a body cavity or lumen as demonstrated in FIG. 3 discussed below.

The center fiber 116 shown in FIG. 2A extends to a distal end of the assembly 102 and has its own end face window assembly 120 in the form of a wide angle lens. This center channel 116 therefore allows the assembly 102 to not only detect infrared radiation along a three dimensional side view region of interest, but also along an end view as well to allow even greater infrared detection in the body cavity or lumen. This may be particularly useful in configurations where the device 100 is endoscopically inserted into a body cavity and the distal end 106 is near abutting or touching a portion of that structure.

In a preferred example, the wide angle lenses 118 are circumferentially staggered about the assembly 102 to collectively provide a 360° side view of a body cavity or lumen and longitudinally staggered to provide a side view along a longitudinal length of at least 5 cm. The length of the longitudinal length may vary, as may the degrees of circumferential coverage.

Figure 3:
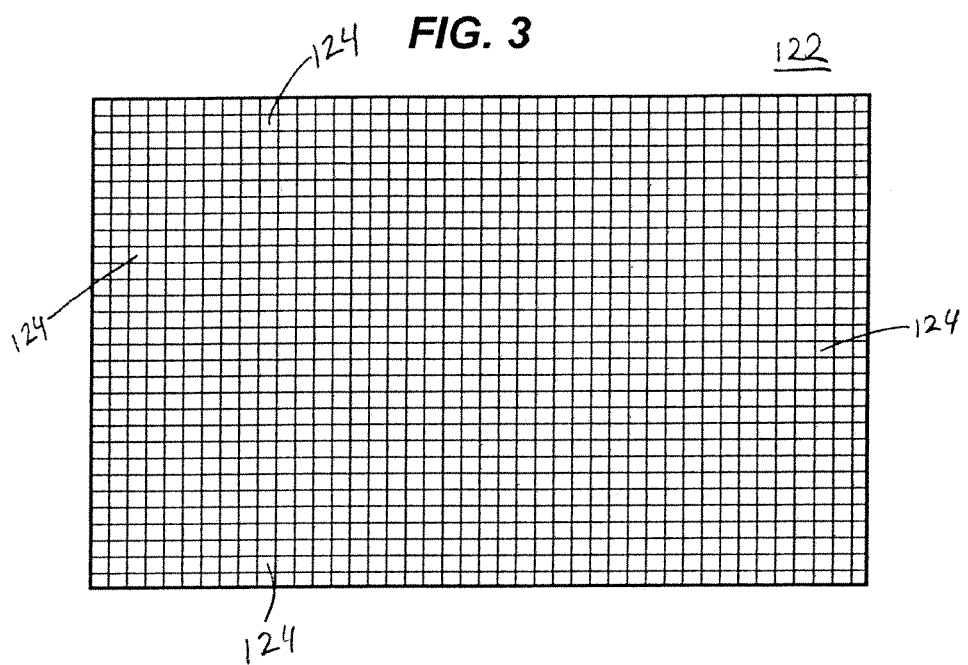
FIG. 3 illustrates an infrared sensor array.

The collected infrared radiation from each of the fiber-optic channels 114 is coupled to the sensor apparatus 108 through lens 112. In the example of FIG. 1B, that lens 112 disperses the collected infrared radiation to cover an infrared sensor 122 which, as illustrated in FIG. 3, is formed of an infrared sensor array of individual pixels 124, only a portion of which are numbered for illustration purposes. The infrared sensor 122 may be formed of any suitable material for use infrared radiation detection. Example materials include indium antimonide, amorphous silicon, mercury zinc telluride, mercury(II) cadmium(II) telluride, lead scandium tantalite, lead zirconate titanate, lead(II) selenide, lead(II) sulfide, germanium, and indium gallium arsenide.

As discussed generally above, the lens 112 may be glued, fused, or otherwise attached to the attachment apparatus 110. The lens 112 may have a concave or convex shape, or the lens 112 may be a gradient-index lens having a varying index of refraction profile across the lens substrate. In yet other examples, the lens 112 may have a diffractive profile for dispersing the collimated incident light from the fiber-optic channel assembly 102. In yet other examples, the lens 112 may be eliminated altogether, allowing the attachment apparatus 110 to couple directly to the infrared sensor 122. In those examples, the device may disperse the collected infrared radiation, if desired, by embedding dispersive lenses within each of the fibers forming the fiber-optic channel assembly 102. For example, each lens in the assembly 102 could be disposed with a cap end having an embedded gradient index lens configuration.

Figure 2B:
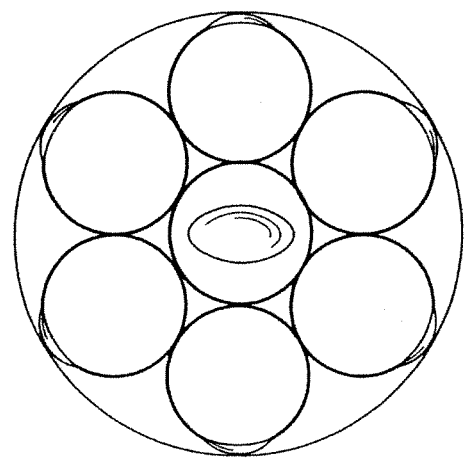
FIG. 2B illustrates an end view of an fiber-optic assembly portion in accordance with another example.

FIG. 2B is similar to FIG. 2A but shows six outer fiber-optic channels (seven channels total) instead of the five outer channels shown in FIG. 2A. That is, in general, the number of fiber-optic channels forming the channel assembly 102 can be varied. As the diameter of each fiber-optic channel decreases, the number of channels in the assembly increases. Smaller diameter channels will limit the size of the wide-angle collection lens, which means that each lens will collect less infrared radiation. However, more lenses may be used and each lens can be designed to have a smaller angle of acceptance in comparison to a larger lens. In general, this demonstrates that variables such as size of the wide-angle lens, the diameter of the fiber-optic channel, the number of fiber-optic channels, and the longitudinal displacement of the lens along the channels can be adjusted to produce an infrared sensor probe of varying size, sensitivity, and collection region of interest (e.g., extending in the longitudinal direction).

Figure 4:
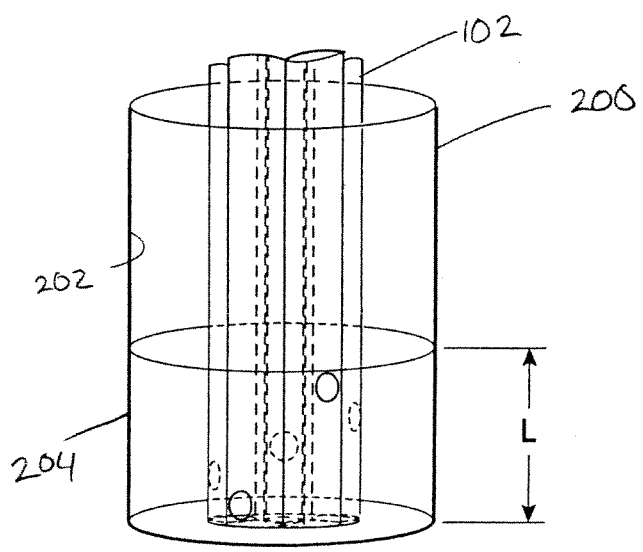
FIG. 4 illustrates the infrared sensor of FIG. 1A deployed in a vessel of a human body.

FIG. 4 illustrates a portion of an esophageal cavity having the endoscopic device 100 positioned therein for detecting infrared radiation around a side view region of interest that extends along a length L and around an entire circumference of an inner wall 202 of the esophagus 200 (all partially shown).

Figure 5:
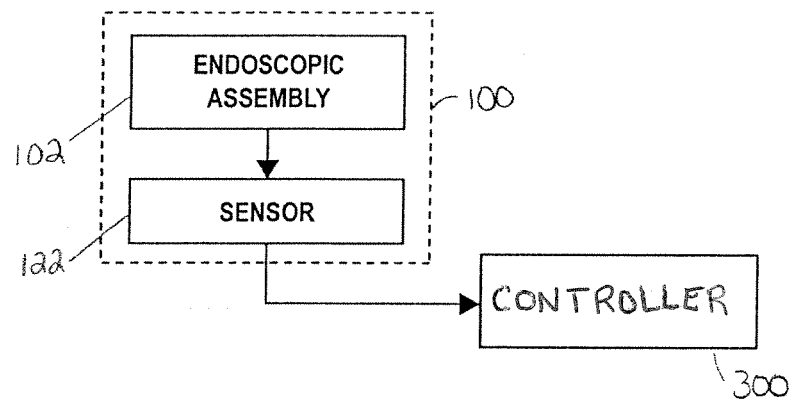
FIG. 5 illustrates a control system for controlling operation of infrared sensing using the sensor of FIG. 1.

The infrared sensor 122 produces an output that is coupled to a signal processor such as a controller 300 as illustrated in FIG. 5. A controller may register each pixel 124 on a grid. During an initial phase, a calibration is performed to develop a base line temperature for infrared reading which is recorded for each of the pixels. For example, the controller 300 may register the baseline pixel readings when the endoscopic device 100 is in a known non-formally affected region of a body cavity or lumen. The controller 300 communicates with the infrared sensor 122 over a continuous cycling or at a sampling frequency that is desired for the way in which the infrared measurements are to be taken. In a preferred example, that sampling frequency may be between 10 and 1000 hertz and would correspond to the loop time associated with detecting and aggregating the infrared signals detected from each of the pixels 124. This sampling frequency would be dependent upon the size of the infrared sensor array, and the number of pixels, as well as on the operating conditions, such as the operating temperature of the sensor array. While infrared sensing technologies have been developed for non-cooled systems, it may be desirable to use cooled infrared sensors for their increased sensitivity and preferred range of infrared wavelengths.

Figure 6:
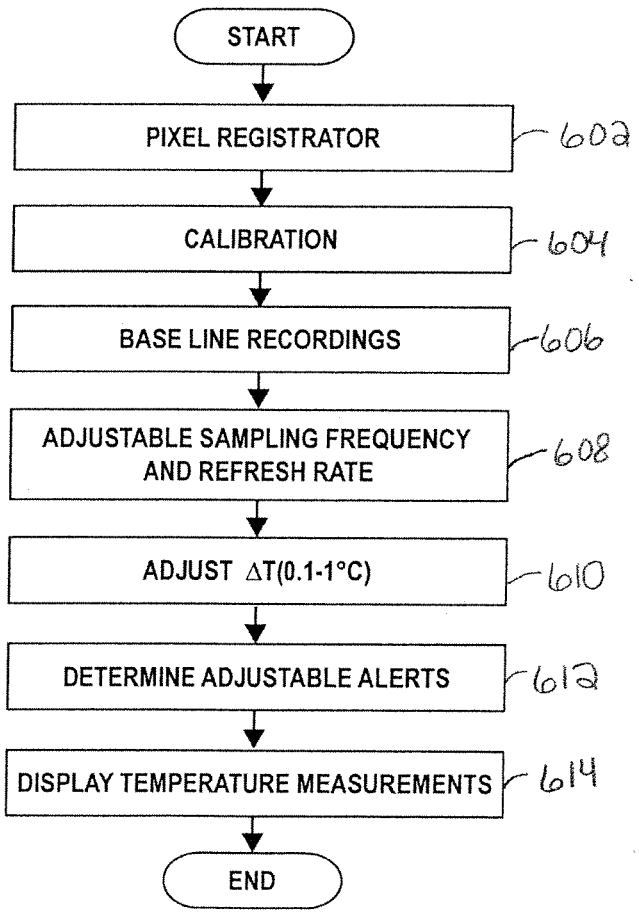
FIG. 6 illustrates a block diagram of a technique for infrared sensing as executed by the control system of FIG. 5, in accordance with an example.

FIG. 6 illustrates a technique 600 that may be executed by the controller 300 in measuring the infrared radiation over an entire side view such as the side view 204 shown in FIG. 4. The controller 300 may be a signal processor in a computer, such as a standalone or networked personal computer or diagnostics machine or terminal. A first block 602 performs a pixel registration to identify the number of pixels in a sensor array. A second block 604 performs a calibration to determine a baseline for reference measurements, which baseline is produced by block 606. A block 608 provides an adjustable sampling frequency and refresh rate that the controller 300 uses to determine the parameters for detecting infrared radiation (or infrared light beams) from the sensor probe.

A block 610 determines temperature data based on the sensed infrared light from the sensor probe. More specifically, block 610 may determine a change in temperature, delta temperature, ΔT, from the base line values from block 606. The granularity of this determination may be set by the controller 300 or user. For example, the block 610 may measure temperature changes from the sensor probe in increments of between 0.1 to 1° C.

Block 612 determines if the temperature data from block 610 is in a temperature region of concern, for example if a high temperature value is above a high temperature threshold for ablation catheter applications, or if a low temperature value is below a low temperature threshold for cryoablation catheter applications. The controller 300 may be programmed to display alert temperature indicators to an operator of the endoscopic device 100 so that as a procedure such as an RF catheter ablation is performed, an alarm is announced when the temperature within the affected esophagus is approaching a potentially detrimental level.

Block 612 may be programmed to identify temporal alerts or other conditions for alerts such as when a certain number of consecutive measurements from the infrared sensor 122 are above a threshold infrared radiation amount. Or the block 612 may trigger based on an absolute time measure, such as when the number of seconds over which a continuous measurement of an infrared radiation exceeds a threshold value.

The block 612 may also be programmed to provide spatial alerts indicating high temperatures. For example, the controller 300 may determine when any pixel or group of sensor pixels (e.g., pixels 124) has an intensity value above a threshold. Or, the block 612 may be programmed to identify when a certain percentage of the overall number of sensor pixels have an intensity value above a threshold level. In some examples, the block 612 may be programmed to determine when a percentage of adjacent pixels have a threshold intensity above a certain amount. In yet other examples, the determination of high infrared readings (and thus high temperatures) may be based on spatial resolution of a change in intensity of infrared radiation. ΔI, delta-intensity, between different pixels or voxels on the sensor. For example, if certain pixels have a ΔI, when compared to other pixel measurements, that is above a threshold change intensity value, then the controller 300 may determine that a high temperature condition exists.

In other words, spatial alarm adjustments may be based on a single pixel, a total number of pixels, a percentage of pixels, or a number of adjacent pixels to determine when it is likely that some portion of the field of interest in the side view of a body cavity has a temperature above a certain threshold amount or a predefined percentage change in temperature compared to a predefined number or percentage of adjacent pixels.

The block 612 also produces a temperature control signal to a subsystem to instruct that subsystem to reduce the temperature. As discussed herein, one such subsystem may be an external ablation-cryoablation controller that receives a temperature control signal from the control 300 to ramp down or completely turn off the ablation/cryoablation device. In other examples, the block 612 may use the temperature control signal, indicating an undesired temperature condition in a vessel, to control a cooling catheter disposed within the vessel and designed to cool down a region of interest experiencing threshold high temperatures. Similarly, the block 612 may use the temperature control signal to control a heating catheter disposed within the vessel and designed to heat up a region of interest experiencing threshold low temperatures.

At block 614 the controller 300 is programmed to map the infrared radiation and display changes in the infrared radiation as detected over the cycle time thereby allowing an operator to visually assess the recorded information as well as being provided a separate alarm in response to the programming of block 612.

Figure 7:
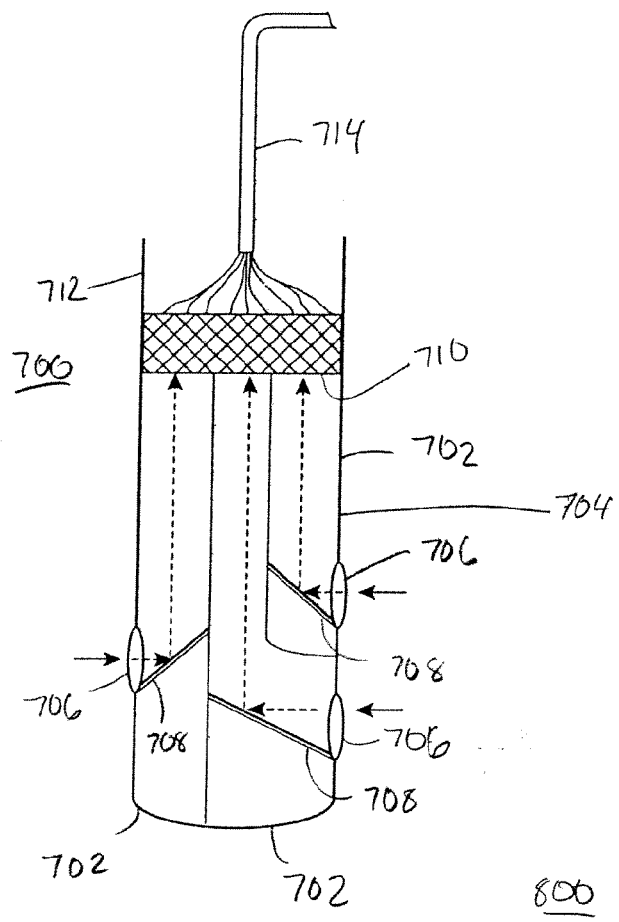
FIG. 7 illustrates an infrared sensor in accordance with another example.

FIG. 7 illustrates another example endoscopic device 700 similar to the device 100 and including a series of fiber-optic channels 702 (only some shown) that are part of an overall fiber-optic channel assembly 704. Each of the channels 702 includes an access window, in this case, a wide angle lens 706, that correspondingly stagger longitudinally and circumferentially about the assembly 704, as discussed above. Each of the fiber-optic channels 702 also includes a mirror 708 that is paired with the wide angle lenses 706 to couple light for infrared radiation from a distal end of the device 700 to a proximal end. In the illustrated configuration, that coupling is coupled directly into an infrared sensor 710 that is internal to the device 700. That is, the device 700 does not need a separate coupling or attachment apparatus or external sensor but rather has a housing body 712 that includes both the sensor and the fiber-optic channel assembly 704.

The infrared signals from the sensor 710 may be coupled to a controller through a wire assembly 714. The outer housing 712 may be a flexible membrane, thereby allowing the device 700 to be easily inserted into a vessel, while at the same time maintaining sufficient mechanical integrity to allow an infrared sensor to be placed directly within the device.

In the configuration of FIG. 7, each of the fiber channels, as well as any fiber channels not shown would be positioned to couple their respective output signals to a different portion of the infrared sensor 710 such that the infrared sensor may be used to resolve the final image of the entire side view of a body cavity or lumen. This coupling may be for the purposes of measuring infrared radiation. However, it would be understood by persons of ordinary skill in the art while reading this disclosure that the infrared sensing described herein may also be used for temperature sensing across the entire side view of the device as well. In this case, the system may be designed to measure an aggregate temperature value over the entire side view or the controller may be programmed to determine an overall average temperature value, a peak temperature value, a change in temperature value, etc., any of which may be used to identify a high temperature alarm condition depending on the particular application.

Figure 8:
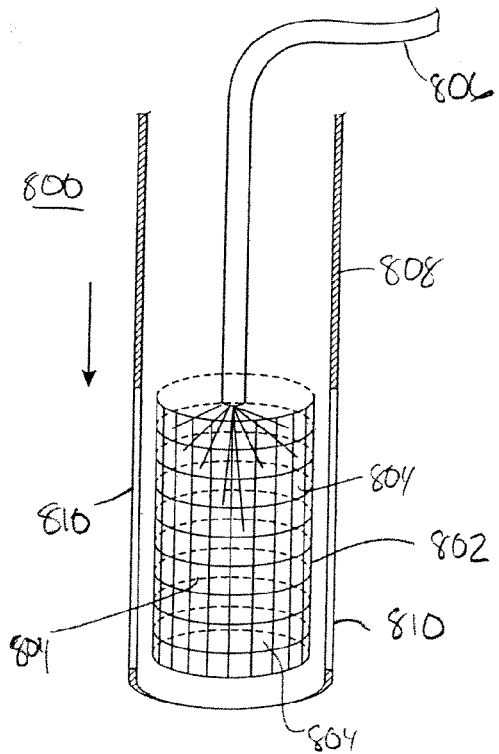
FIG. 8 illustrates an infrared sensor in accordance with yet another example.

FIG. 8 illustrates another example configuration of an endoscopic device 800 that is able to detect infrared radiation over an entire side view or area of interest within a body cavity or lumen. However, the device does not rely on individual fiber-optic channels bundled together. Nor does the device rely on staggered access windows or wide angle lenses. But rather the device 800 includes a cylindrical infrared sensor array 802 having a plurality of pixels 804 that are configured in a cylindrical shape extending along a longitudinal axis of the device 800. Each of the pixels 804 may be a micro infrared sensor individually capable of detecting infrared radiation over a portion of a side view of interest.

By configuring the pixels in an array configuration around the cylinder of the sensor 802, an entire three dimensional volume may be measured. Each individual sensor 804 couples its detected infrared signal into a wire assembly 806 connected to a controller for infrared data processing. The device 800 includes a flexible membrane 808 with a window layer 810 transparent or substantially transparent over the infrared spectral region of interest. The window 810 protects the sensor 802 from direct contact with a vessel and protects the sensor 802 from any constraints or debris within the same. Example materials that may be used for the membrane 808 and the transparent layer 810 include acrylics, polycarbonates, polyurethanes, nylons, cyclic olefin polymers, polyesters, high refractive index polymers. Such materials may also be used for forming a thin outer casing or housing for the other examples described herein. The materials used for the sensor 802 may be those discussed herein.

Figure 9:
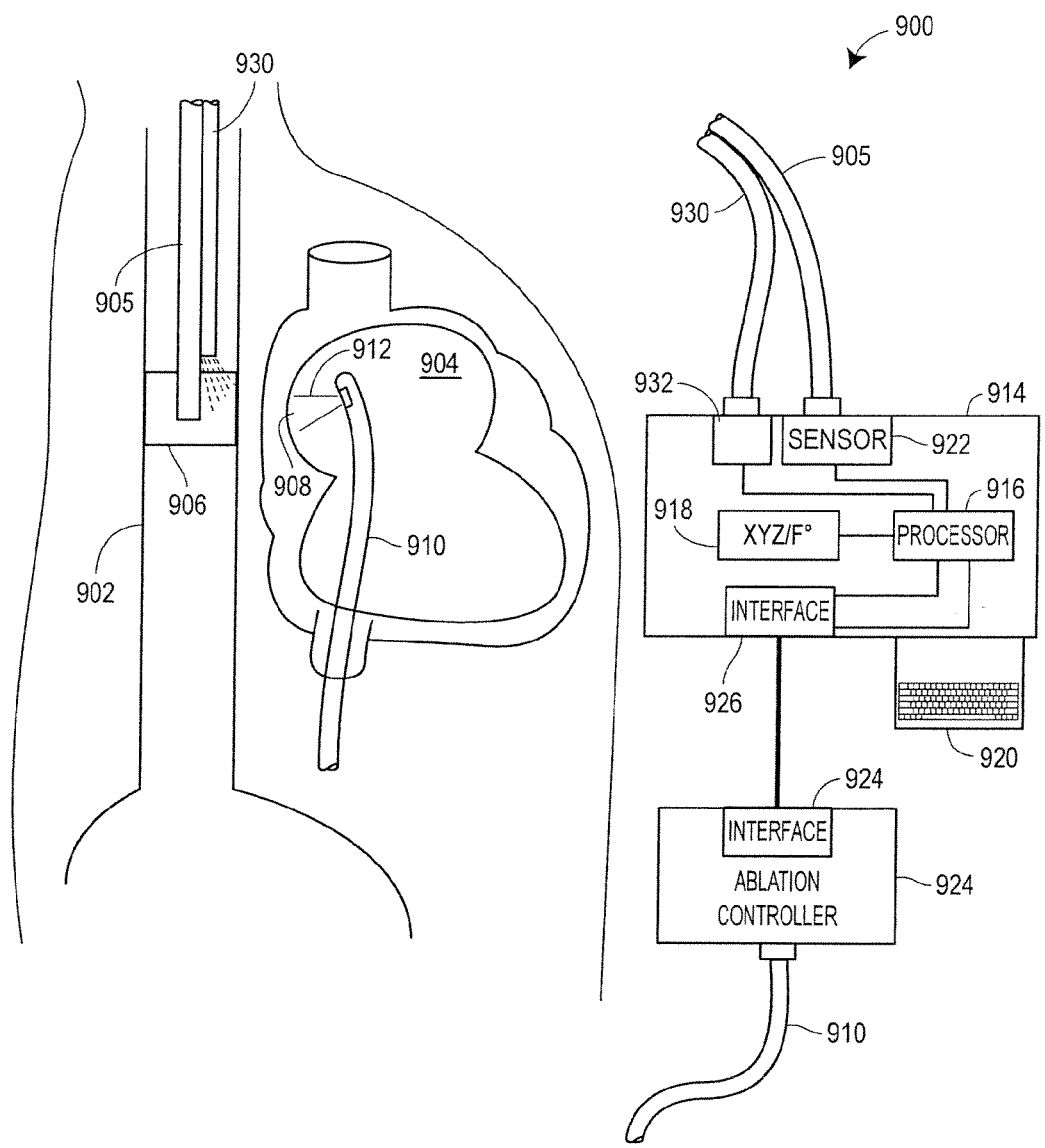
FIG. 9 illustrates an example feedback control of an ablation catheter using an infrared sensor.

FIG. 9 illustrates an example application in accordance with the above descriptions, and in particular showing an endoscopic infrared sensor device 900 positioned within an esophagus 902 at a location near where the esophagus 902 is adjacent another body cavity, in this instance the left atrium 904. As discussed above, the two cavities 902 and 904 will abut over some region, for example, over a length of up to 5-6 cm and a width of up to 4-5 cm depending on patient physiology. The sensor device 900 has an infrared sensor probe 905 that is positioned to measure infrared radiation corresponding to the thermal temperature of a region of interest 906 extending around an inner wall of the esophagus 902. More specifically, the probe 905 is positioned to measure infrared radiation over a region the coincides with a region of interest 908 in the left atrium 904 over which an energy treatment is being applied, for example, as part of an atria arrhythmia treatment procedure.

An energy application catheter 910 (or subsystem) is positioned in the left atrium 904 and may apply radiation such as visible, UV. IF, coherent laser energy or non-coherent emissions, RF energy, microwave energy, ultrasonic energy, chemical treatment, resistive heating, or other energy types to the region of interest 908. In the illustrated example the catheter 910 is an ablation catheter applying RF ablation energy 912 to the region of interest 908, for example, for treatment of arrhythmia. The ablation catheter 910 may be about 4 mm in diameter. Although the details are not shown, the catheter 910 may be an irrigated, cooled catheter with sufficient shielding to concentrate application of the ablation energy without providing damage or discomfort over regions of the catheter's length proximal to the ablation end tip.

The ablation catheter 910 is to be inserted into the left atrium using standard techniques. Generally speaking, patients are given a local anesthetic and are sedated through intravenous medication (or may receive general anesthesia). The catheter 910 is inserted into the femoral vein in the groin and tracked using x-ray guidance from the groin into the heart. The catheter 910 is then advanced into the left atrium 904 through a transeptal puncture (as has been widely published previously or through a patent foramen ovale. Those of ordinary skill in the art will appreciate that other insertion techniques may be employed. In contrast to the catheter 910, the probe 905 is generally administered orally through the mouth and into the esophagus 902, and can be a passive catheter or a steering catheter device. While endocardial ablation techniques are described hereinabove, it will be appreciated that endocardial ablation techniques may be used instead and similarly integrated into a feedback control configuration with the sensor probes assemblies described herein.

The probe 910 is connected to a control apparatus 914 that includes a processor 916 for controlling, among other things, the power output of the probe 910. The apparatus 914 may thus be a processor controlled machine executing instructions to control operation of the probe 910. The apparatus 914 may optionally include a display 918 for providing visual indications to a user, such as operating power levels, temperature readings, and/or images of the left atrium 904 if an endoscopic imaging probe is used. The apparatus 914 further includes an input device 920, such as a keyboard, GUI interface touch screen, touch pad, handheld device, etc. that allows a user to input power setting levels, temperature thresholds, patient data, etc. The input device 920 may be integrated with the display 918.

To prevent left atrial ablation from inducing necrosis or damage to the esophageal wall leading to fistula formation, the probe 905—any of the infrared sensor probes described herein may be used—senses the thermal conditions in the esophagus 902 resulting from the ablation treatment in the left atrium 904. In an example, infrared radiation is collected by the probe 905 and fed to a sensor 922 connected to the processor 916 which may execute instructions to determine temperature measurements from the esophagus 902. For example, the processor 916 may determine a maximum measured temperature in the esophagus 902, in response to which the processor 916 may compare that maximum temperature to a baseline calibration temperature or a threshold temperature to determine the amount of temperature change in the esophagus 902 and/or whether the temperature at a location in the esophagus 902 has increased beyond a threshold amount. The temperature threshold value may be provided by a user through the input device 920, for example. If the processor 916 determines that the sensed temperature is above a temperature threshold indicating potential damage to the esophageal wall, then the processor 916 may indicate a warning signal on the display 918 to identify the undesired temperature range to the user. The processor 916 may then communicate with an ablation device controller 924 to provide data instructing that controller to reduce the ablative RF energy 912 applied to the left atrium 904. The controller 924 is part of a dedicated ablation delivery assembly in the illustrated application and is interfaced with the probe controller 914 through data communication interfaces (or ports) 926 and 928. The processor 916 may be designed to provide a turn-off instruction to the controller 924, such that in response the controller 924 turns off the ablation energy source 924 altogether. This turn-off condition, whether controlled by deference to controller 914 as the master controller or by the controller 924 directly, is useful when the temperature increase is such that necrosis or esophageal damage appears imminent. In some such examples, the control apparatus 914 may apply different threshold levels such that at a low temperature threshold only a warning indication is provided to the user (e.g., color coding a temperature value or temperature indication insignia); but when the temperature value increases past a high threshold level, the control apparatus 914 sends a turn-off signal to the controller 924.

In some examples the probe 910 may have its own feedback control using a temperature sensor within the left atrium 904. In such instances, the processor 916 would control probe operation based on multiple temperature sensors, one of the vessel being affected (e.g., the left atrium 904) and the other for an adjacent vessel (e.g., the esophagus 902) containing the infrared sensor. In any event, in these examples the infrared sensor may be used to automatically control the amount of treatment energy applied during a procedure in an adjacent body cavity.

In other examples, both the infrared sensor probe and the ablation probe may be used in the same bodily cavity to as part of a feedback control.

The device 900 is also shown with an alternative apparatus for preventing heat damage to the esophagus 902. The sensor probe 905 is shown with an optional application catheter 930 (cooling subsystem) or lumen that is connected to an applicant source 932 and controlled by apparatus 914 to release the applicant to the region of interest 906, upon detection of a high temperature condition. For example, the catheter 930 may have an opening at a distal end at the point of the wide angle lens of the sensor probe 905 and which releases cool water, liquid nitrogen, or another cooled fluid designed to reduce the temperature in the esophagus 902 upon contact. Preferably, the opening would be configured to create a spray effect where the cooling fluid is contacted over the entire region of interest 906, as the particular location of the excessive temperature over the region of interest may not be known. In other examples, the opening may extend around only a portion of the circumference of the probe 905, i.e., less than 360°, but where the opening is facing the heart side of the esophagus 902. Preferably, the opening is designed to result in the fluid being applied along the longitudinal axis of the esophagus 902 as well. The amount of applicant fluid used is controlled by the control apparatus 914, and may be delivered as a continuous application or through intermittent, pulsed applications of fluids. In some examples, the applicant fluid may be delivered in one or more puffs sufficient enough to cool the high temperature region.

The catheter 930 may be a dedicated device fused to, bonded to, otherwise attached to, the sensor probe catheter 905. In other examples, the catheter 930 may be implemented as an outer lumen shell surrounding the probe 905 from a proximal end at the control apparatus 914 to a distal end that is near but short of the distal-most end over which infrared detection occurs. The catheter 930 may be controlled by the control apparatus 914 or separately from the control of the probe 905.

In cryoablation applications, the catheter 930 may be a heating subsystem designed to apply a heating fluid to the esophagus 902 to avoid thermal damage.

Preferably, the sensing probes described herein are disposable devices, either single use or limited use assemblies to better ensure biological inertness and medical safety. The entire catheter device may be disposable, or each probe sensor may have an outer sheath that is disposable after a single use. The sheath would be formed of an infrared transparent material, but one that can be easily removed from the underlying sensor probe. In some examples, the sensing probes can be restricted use devices that must be registered with a control apparatus 914 prior to operation. The control apparatus 914 therefore may selectively enable or disable probes from operation based on whether there has been a proper registration of a probe. Such registration may be achieved through sensor probes with embedded identification chips at the connector end where the probe engages the control apparatus, through bar code scanning, or other known registration techniques. Such techniques are useful in that they can limit the amount of time between which a sensor probe has been registered and when the sensor probe is used in a medical procedure, and do so separately from their ability to limit the number of times a sensor probe can be used.

Alternatively to ablation, the catheter 910 may be a cryoablation device used to destroy cardiac tissue and thereby eliminate arrhythmogenic foci. In such an example, the probe 905 would be configured to monitor for excessive decreases in temperature in the esophagus 902 and resulting from cryoablation application in the left atrium 904. In fact, an advantage of the some implementations of the present techniques is that a single infrared probe device may be used for ablation or cryoablation applications by using a controller that identifies both excessively high and excessively low temperatures based on the IF values sensed by the probe sensor array.

While the examples described herein are described in the context of an infrared sensor device, the sensors may be used for non-thermal detection applications such that non-infrared radiation may be detected instead. The optic fiber channels may collect light across a range of frequencies, i.e., UV, visible, near-infrared, far-infrared, and which may be used by a processor to determine physical characteristics within a body cavity. In some examples, sensor probes as described herein may be combined with light sources that illuminate a portion of a body cavity, where reflected light or fluorescence, etc. may then be sensed by an optic fiber channel assembly capable of measuring across a volume of interest to determine characteristics of the cavity. For example, during a chemical treatment, a light source may be used to illuminate a treatment region of interest, and a sensor may measure for radiation over a characteristic spectral region, or regions, corresponding to that treatment chemical to determine if it is present in the region of interest.

In these or any other examples described herein an optical filter element may be used to selectively pass only a region of wavelengths to the infrared (or other) sensor apparatus. This may improve signal-to-noise ratios in the sensor apparatus, as well as reduce affects such as blooming or flashes than can occur with infrared sensors. Of course, these and other techniques for optimizing measurement of the collected radiation will be known and thus are not further described herein.

Various modifications and implementations will be apparent to persons of ordinary skill in the art based on the foregoing. For example, while fiber-optic channels are illustrated as having a single window, or wide-angle lens, for collecting infrared radiation, it will be appreciated that each channel may have multiple windows for radiation collection. Furthermore, while multiple channels are illustrated in some examples, it will be appreciated that fewer channels may be used, and in fact that one or more channels may be sufficient, where those one or more channels may each have one or more infrared radiation windows.

At least some of the various blocks, operations, and techniques described above may be implemented in hardware, firmware, software, or any combination of hardware, firmware, and/or software. When implemented in software or firmware, the software or firmware may be stored in any computer readable memory such as on a magnetic disk, an optical disk, or other storage medium, in a RAM or ROM or flash memory, processor, hard disk drive, optical disk drive, tape drive, etc. Likewise, the software or firmware may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software or firmware may be delivered to a user or a system via a communication channel such as a telephone line, a DSL line, a cable television line, a fiber-optics line, a wireless communication channel, the Internet, etc. (which are viewed as being the same as or interchangeable with providing such software via a transportable storage medium). The software or firmware may include machine readable instructions that are capable of causing one or more processors to perform various acts.

Although the present invention has been described in several embodiments, a myriad of changes, variations, alterations, transformations, and modifications may be suggested to one skilled in the art, and it is intended that the present invention encompass such changes, variations, alterations, transformations, and modifications as falling within the spirit and scope of the appended claims.

What is claimed:

1. An endoscopic device for measuring infrared radiation in a vessel, the endoscopic device comprising:
   an infrared sensor array; and
   a fiber-optic channel assembly for communicating infrared radiation to the infrared sensor array, the fiber-optic channel assembly including,
   a distal end having an end face for collecting infrared radiation along an end view, and
   a plurality of lenses disposed on a periphery of the fiber-optic channel assembly for collecting infrared radiation along a side view, where the plurality of lenses are longitudinally staggered along a length of the fiber-optic channel and circumferentially staggered around the periphery forming a helical path to collect infrared radiation over a two dimensional area forming the side view, and where the plurality of lenses have sufficiently wide-angle views so as to collectively provide a 360-degree view of circumferential coverage.

2. The endoscopic device of claim 1, wherein the fiber-optic channel assembly comprises a plurality of fiber-optic channels each including one of the plurality of lenses and each including an angle reflector for reflecting the infrared radiation collected by the respective lens along a longitudinal axis of the fiber-optic channel.

3. The endoscopic device of claim 2, wherein each of the plurality of fiber-optic channels is disposed to provide each respective infrared beam to a different portion of the infrared sensor array, where the infrared sensor array is to produce an infrared data signal in response to the infrared beams from the fiber-optic channels, and where that infrared data signal is to be used to determine a temperature condition of the side view.

4. The endoscopic device of claim 3, further comprising a center fiber extending to the distal end of the fiber-optic channel assembly and having the end face, wherein the plurality of fiber-optic channels surround the center fiber, and wherein the center fiber is disposed to provide a respective infrared beam to the infrared sensor array for producing the infrared data signal in response to the infrared beams from the fiber-optic channels and from the center fiber.

5. The endoscopic device of claim 3, further comprising a control apparatus coupled to receive the infrared data signal from the infrared sensor array and to determine the temperature condition of the side view.

6. The endoscopic device of claim 5, wherein the control apparatus comprises:
   a processor; and
   a computer-readable medium having computer-executable instructions that, when executed, cause the processor to:
   a) determine temperature data for the side view in response to the infrared data signal; and
   b) determine if the temperature data is in a temperature region of concern in the vessel.

7. The endoscopic device of claim 6, wherein the temperature region of concern is when a determined high temperature value for the vessel is above a high temperature threshold.

8. The endoscopic device of claim 6, wherein the temperature region of concern is when a determined low temperature value for the vessel is below a low temperature threshold.

9. The endoscopic device of claim 6, wherein the computer-readable medium has computer-executable instructions that, when executed, cause the processor to c) provide a temperature control signal to a subsystem to instruct the subsystem to reduce temperature in the vessel.

10. The endoscopic device of claim 9, wherein the subsystem is an ablation catheter in an adjacent vessel.

11. The endoscopic device is of claim 9, wherein the subsystem is an applicant catheter in the vessel and connected to a fluid source having a cooling fluid that when applied to the vessel reduces the temperature in the vessel.

12. The endoscopic device of claim 6, wherein the computer-readable medium has computer-executable instructions that, when executed, cause the processor to c) calibrate the infrared sensor array to sense the respective infrared beams and to provide the infrared data signal.

13. The endoscopic device of claim 2, wherein the plurality of lenses are longitudinally staggered to provide the side view along a longitudinal length of the vessel, where that longitudinal length is greater than about 5 cm.

14. The endoscopic device of claim 1, wherein the infrared sensor array is external to the fiber-optic channel, the endoscopic device further comprising an attachment lens for coupling the infrared radiation from the fiber-optic channel assembly to the infrared sensor array.

15. The endoscopic device of claim 1, wherein the infrared sensor array is integrally coupled to the fiber-optic channel, the endoscopic device further comprising a housing membrane enclosing the fiber-optic channel and the integrally coupled infrared sensor array.

16. The endoscopic device of claim 1, wherein the endoscopic device is sized so as to be administered orally to reach the vessel.

17. A method of determining temperature in a vessel using an endoscopic device having a distal end, the vessel having a side volume of interest that extends longitudinally along the vessel and over at least a portion of an inner radial extent of the vessel, the method comprising:
   positioning a plurality of outer fibers surrounding a center fiber;
   disposing a plurality of infrared radiation collection elements longitudinally along the endoscopic device, and circumferentially about the endoscopic device, in a helical manner, with one of the plurality of radiation collection elements on each of the plurality of outer fibers; and
   coupling the plurality of infrared radiation collection elements to an infrared sensor array via the plurality of outer fibers for detecting temperature over the side volume of interest.

18. The method of claim 17, wherein the side volume of interest extends 360°.

19. The method of any of claim 17, further comprising collecting infrared radiation along an end view of the endoscopic device through an end face at a distal end of the endoscopic device.

20. An endoscopic device for measuring infrared radiation in a vessel, the endoscopic device comprising:
   an infrared sensor array;
   a dispersing lens; and
   a fiber-optic channel assembly for positioning in the vessel and for communicating infrared radiation collected from the vessel to the infrared sensor array via the dispersing lens, where the fiber-optic channel assembly is adapted to passively collect infrared radiation from the vessel, the dispersing lens is adapted to disperse the collected infrared radiation to cover the infrared sensor array, and the infrared sensor array is adapted to detect the dispersed infrared radiation, the fiber-optic channel assembly including, a distal end having an end face for passively collecting infrared radiation along an end view, and a plurality of lenses disposed on a periphery of the fiber-optic channel assembly for passively collecting infrared radiation along a side view, where the plurality of lenses are longitudinally staggered along a length of the fiber-optic channel and circumferentially staggered around the periphery forming a helical path to passively collect infrared radiation over a two dimensional area forming the side view.

21. The endoscopic device of claim 20, wherein the infrared sensor array is (i) adapted to receive the passively collected infrared radiation from the end face and from the two dimensional area forming the side view and (ii) adapted to produce an infrared data signal indicative of a temperature condition in the vessel.

22. The endoscopic device of claim 20, wherein the infrared sensor array is an infrared camera adapted to produce a temperature map of the vessel.

\* \* \* \* \*

UNITED STATES PATENT AND TRADEMARK OFFICE
CERTIFICATE OF CORRECTION

PATENT NO. : 8,971,997 B2
APPLICATION NO. : 12/934008
DATED : March 3, 2015
INVENTOR(S) : Hakan Oral et al.

It is certified that error appears in the above-identified patent and that said Letters Patent is hereby corrected as shown below:

In the Claims:

At Column 14, line 8, Claim 11, "device is of" should be -- device of --.

At Column 14, line 54, Claim 19, "of any of" should be -- of --.

Signed and Sealed this
Eighth Day of December, 2015

Michelle K. Lee
*Director of the United States Patent and Trademark Office*